United States Patent
Langston

(10) Patent No.: US 9,332,914 B2
(45) Date of Patent: *May 10, 2016

(54) COAXIAL DUAL LUMEN PIGTAIL CATHETER

(71) Applicant: Phil Langston, Mounds, OK (US)

(72) Inventor: Phil Langston, Mounds, OK (US)

( * ) Notice: Subject to any disclaimer, the term of this patent is extended or adjusted under 35 U.S.C. 154(b) by 224 days.

This patent is subject to a terminal disclaimer.

(21) Appl. No.: 14/076,730

(22) Filed: Nov. 11, 2013

(65) Prior Publication Data

US 2014/0187933 A1    Jul. 3, 2014

Related U.S. Application Data

(60) Continuation of application No. 11/890,070, filed on Aug. 3, 2007, now Pat. No. 8,613,706, which is a division of application No. 10/797,583, filed on Mar. 10, 2004, now abandoned.

(51) Int. Cl.
 *A61B 5/02* (2006.01)
 *A61B 5/0215* (2006.01)
 *A61B 5/00* (2006.01)

(52) U.S. Cl.
 CPC ........... *A61B 5/0215* (2013.01); *A61B 5/02158* (2013.01); *A61B 5/6857* (2013.01)

(58) Field of Classification Search
 None
 See application file for complete search history.

(56) References Cited

U.S. PATENT DOCUMENTS

| | | | |
|---|---|---|---|
| 4,747,840 A | 5/1988 | Ladika et al. | |
| 4,770,652 A | 9/1988 | Mahurkar | |
| 4,777,951 A * | 10/1988 | Cribier et al. | 606/194 |
| 4,961,731 A * | 10/1990 | Bodicky et al. | 604/264 |
| 5,009,234 A | 4/1991 | Alt | |
| 5,016,808 A | 5/1991 | Heil, Jr. et al. | |
| 5,037,403 A | 8/1991 | Garcia | |
| 5,041,084 A | 8/1991 | DeVries et al. | |
| 5,052,998 A | 10/1991 | Zimmon | |
| 5,059,177 A | 10/1991 | Towne et al. | |
| 5,308,318 A | 5/1994 | Plassche, Jr. | |
| 5,346,471 A | 9/1994 | Raulerson | |
| 5,380,270 A | 1/1995 | Ahmadzadeh | |
| 5,380,276 A | 1/1995 | Miller et al. | |
| 5,480,380 A | 1/1996 | Martin | |
| 5,480,392 A | 1/1996 | Mous | |
| 5,603,705 A * | 2/1997 | Berg | 604/527 |
| 5,683,640 A | 11/1997 | Miller et al. | |

(Continued)

OTHER PUBLICATIONS

Application and File History for U.S. Appl. No. 11/890,070, filed Aug. 3, 2007. Inventors: Phil Langston.

(Continued)

*Primary Examiner* — Etsub Berhanu
*Assistant Examiner* — Karen Toth
(74) *Attorney, Agent, or Firm* — Patterson Thuente Pedersen, P.A.

(57) ABSTRACT

A coaxial dual lumen pigtail catheter utilizes coaxial construction incorporating a thin wall guiding catheter technology for the outer lumen and using a strong braided diagnostic technology for the central lumen to accommodate high-pressure injections. The catheter includes a manifold body to provide for connection to each of the dual lumens. The distal end of the coaxial dual lumen pigtail catheter tapers to a more flexible portion that is perforated by spiral side holes to provide for more undistorted pressure readings in the left ventricle. The coaxial dual lumen pigtail catheter also utilizes proximal straight sideholes at the end of the dual lumen portion and a taper between the dual lumen portion and the single lumen portion.

21 Claims, 3 Drawing Sheets

(56) References Cited

U.S. PATENT DOCUMENTS

| | | | |
|---|---|---|---|
| 5,961,485 | A | 10/1999 | Martin |
| 5,976,103 | A * | 11/1999 | Martin .......................... 604/43 |
| 6,048,332 | A | 4/2000 | Duffy et al. |
| 6,332,892 | B1 | 12/2001 | Desmond, III et al. |
| 6,413,228 | B1 | 7/2002 | Hung et al. |
| 6,508,789 | B1 | 1/2003 | Sinnott et al. |
| 6,656,146 | B1 | 12/2003 | Clayman et al. |
| 8,613,706 | B2 * | 12/2013 | Langston ...................... 600/486 |
| 2002/0173693 | A1 | 11/2002 | Landesberg |
| 2003/0195409 | A1 | 10/2003 | Seitz et al. |
| 2003/0199779 | A1 | 10/2003 | Muhlenberg et al. |
| 2004/0254483 | A1 | 12/2004 | Zdeblick et al. |
| 2006/0144155 | A1 * | 7/2006 | Liu ................................ 73/753 |
| 2007/0161914 | A1 | 7/2007 | Zdeblick et al. |
| 2007/0219591 | A1 | 9/2007 | Zdeblick et al. |

OTHER PUBLICATIONS

Application and File History for U.S. Appl. No. 10/797,583, filed Mar. 10, 2004. Inventors: Phil Langston.

* cited by examiner

COAXIAL DUAL LUMEN PIGTAIL CATHETER

RELATED APPLICATION

This application is a continuation of application Ser. No. 11/890,070 entitled "Coaxial Dual Lumen Pigtail Catheter" filed Aug. 3, 2007, which in turn is a divisional of application Ser. No. 10/797,583 entitled "Coaxial Dual Lumen Pigtail Catheter" filed Mar. 10, 2004, now abandoned, each of which is hereby fully incorporated herein by reference.

FIELD OF INVENTION

The present invention relates generally to the field of cardiac catheters. More specifically, the invention relates to cardiac catheters for performing procedures for the testing of aortic stenosis.

BACKGROUND OF THE INVENTION

Aortic stenosis is a condition in which the aortic valve has become stenotic (narrowed) and does not open normally. The aortic valve is located between the left ventricle of the heart and the aortic arch. The aortic arch leads to the ascending and descending aorta as well as other major blood vessels and is the main blood vessel that supplies oxygen rich blood to the rest of the body. When the aortic valve is stenotic, the ability of the left ventricle to pump blood out of the heart into the aorta and other arteries is impaired. The body's organs including the brain may then receive an insufficient supply of oxygen rich blood and blood may tend to back-up into the lungs causing shortness of breath.

The aortic valve is a tricuspid valve. That is, it has three leaflets or flaps that open and close. The function of the aortic valve is to allow blood to flow only out of the left ventricle and into the aorta when the left ventricle is contracting. When the heart muscle relaxes, the aortic valve closes, thus preventing blood from the aorta from flowing back into the left ventricle. When a patient has aortic stenosis, the leaflets of the aortic valve become thickened and calcified. Historically, a common cause of aortic stenosis was patients who had rheumatic fever during childhood. Other patients developed symptoms of aortic stenosis when they are in their 40's or 50's because of a genetically determined defect in which the aortic valve has two leaflets instead of three. By far, the most common cause of aortic stenosis is age related degeneration and calcification of the aortic valve. Typically, degenerative aortic stenosis begins to manifest symptoms when patients are more than 70 years old.

When the aortic valve becomes stenotic, the volume of blood pumped out of the left ventricle is reduced. The heart tissue then tends to hypertrophy to compensate for the increased effort necessary to pump blood out of the left ventricle. This ventricular hypertrophy leads to an enlarged heart. Ultimately, the left ventricle looses flexibility, tends to dilate and becomes even less efficient at pumping blood into the aorta. In some cases, the aortic valve becomes so stenotic that blood flow to the brain is dramatically reduced causing syncope. In addition, aortic stenosis patients often suffer from angina. Finally, patients with aortic stenosis tend to demonstrate shortness of breath because of the accumulation of blood in the lungs. Patients with severe aortic stenosis may require replacement of the aortic valve with a prosthetic heart valve.

One way to gauge the severity of aortic stenosis is to measure the pressure differential between the left ventricle and the aortic arch, across the aortic valve. Measuring differential pressure across the aortic valve to diagnosis aortic stenosis is a known procedure. One such technique for measuring differential pressures across the aortic valve utilizes a catheter that has an eight French diameter along its entire length and two parallel side-by-side lumens of unequal size. This catheter incorporates a perforated metal plate in the distal segment of the smaller lumen that allows fluid communication for measuring pressure in the aorta. The larger lumen of this catheter incorporates distal side holes that allow fluid communication for measuring pressure in the left ventricle. The smaller lumen is perforated on one side only and can lead to distorted pressure reading if the perforations impinge on the wall of the aorta as the pressure wave of aortic systole moves past the catheter. The side-by-side arrangement of the catheter tends to make the catheter less flexible and more difficult to maneuver. In addition, the durometer of the eight French distal tip is not always soft enough to conform to a guide wire.

Pigtail catheters are known in the art. A pigtail is a coiled or spiral portion at the terminal end of a catheter. The coil generally approximates three hundred sixty degrees but may be somewhat more or less than this value. A pigtail design presents a blunt, smooth, resilient end to body tissue into which it comes in contact reducing the risk of damage to tissues that the end of the catheter comes into contact with.

It would be a benefit to the diagnostic arts if there was available a differential pressure measuring catheter that was flexible enough to consistently conform to a guide wire and whose pressure measuring qualities were less effected by impingement on the vascular tissues.

SUMMARY OF THE INVENTION

The coaxial dual lumen pigtail catheter for performing testing in aortic stenosis addresses the above problems. The invention utilizes coaxial construction incorporating a thin wall extrusion for the outer lumen and using a strong braided extrusion for the central lumen and high-pressure injections. The catheter of the present invention includes a manifold body to provide for connection to each of the two lumens. The distal end of the coaxial dual lumen pigtail catheter tapers to a more flexible portion that is perforated by spiral side holes around at least a substantial portion of the circumference of the catheter to provide for less distorted pressure readings and to allow for perfusion into the left ventricle.

The coaxial dual lumen pigtail catheter of the present invention generally includes a dual lumen portion, single lumen portion and a pigtail portion. Preferably, the dual lumen portion is sized to be either an eight French or more preferably seven or even six French in diameter. Preferably, the single lumen portion has a five French diameter and the pigtail portion has a five French diameter. The coaxial dual lumen pigtail catheter utilizes proximal straight sideholes at the end of the dual lumen portion and a taper between the dual lumen portion and the single lumen portion. At the distal end of the single lumen portion, but proximal to the pigtail are located additional sideholes. These sideholes provide a conduit for taking a pressure measurement within the left ventricle as well as providing a conduit for the injection of diagnostic fluids, if necessary. Desirably, the sideholes are arranged in a spiral pattern around the single lumen portion.

DETAILED DESCRIPTION OF THE INVENTION

Figure 1:
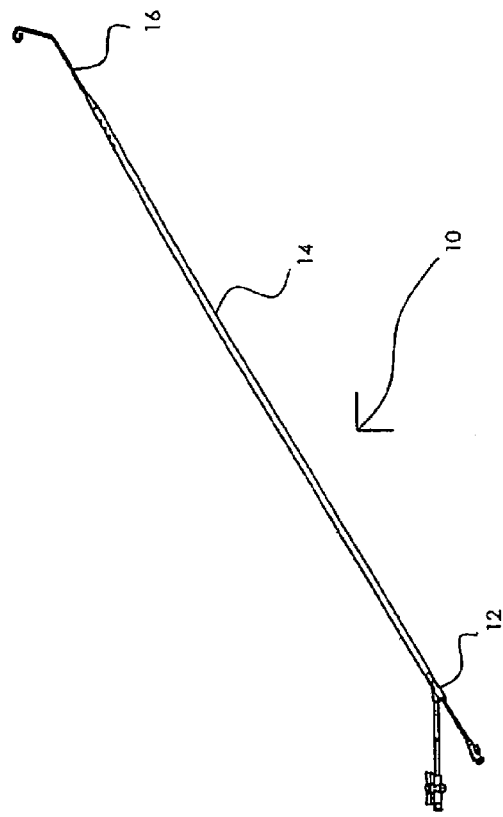
FIG. 1 is a perspective view of a coaxial dual lumen pigtail catheter.

Referring to FIG. 1, the coaxial dual lumen pigtail catheter 10 (catheter 10) generally includes manifold portion 12, dual lumen portion 14 and single lumen portion 16.

Figure 2:
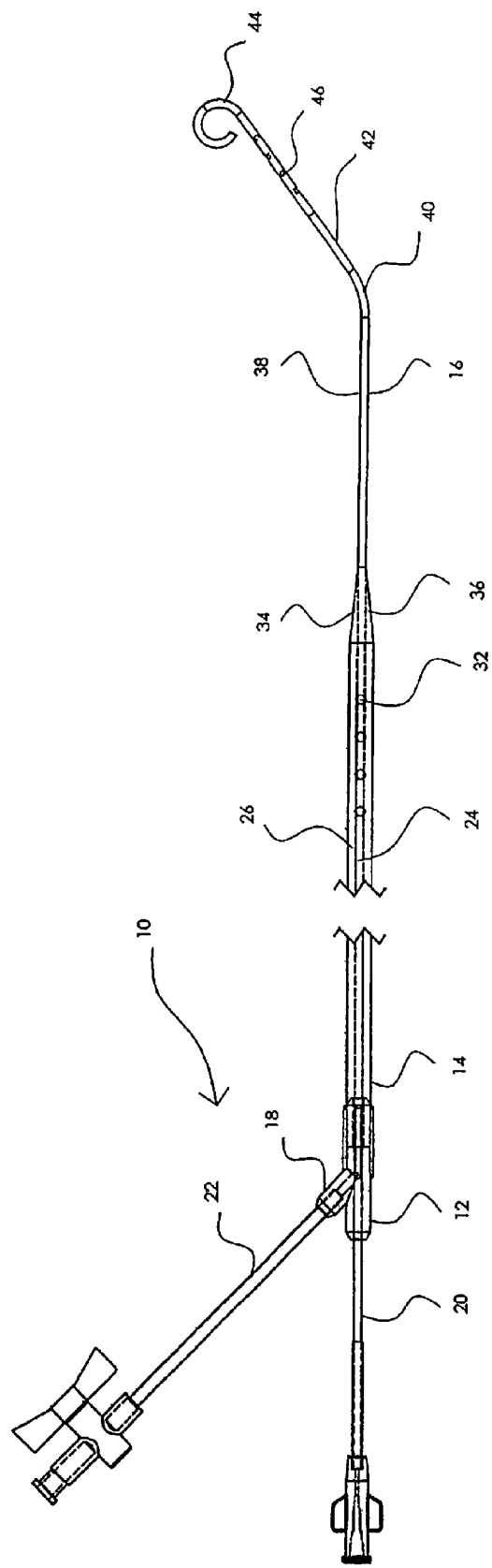
FIG. 2 is a plan view of the coaxial dual lumen pigtail catheter of the present invention, including phantom lines showing the interior lumen.
Figure 4:
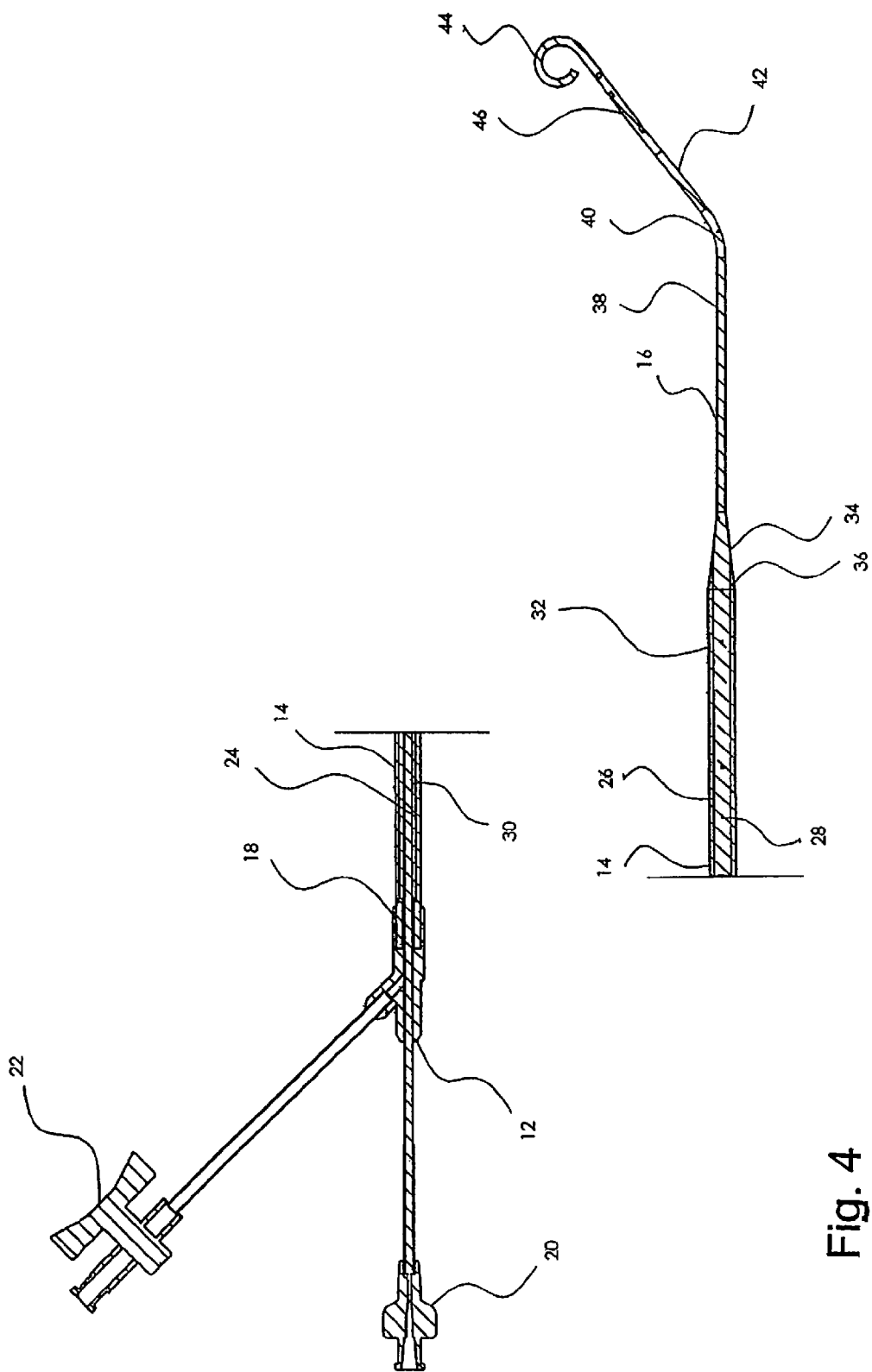
FIG. 4 is a sectional view of the coaxial dual lumen pigtail catheter.

Manifold portion 12 includes manifold body 18, first connector 20 and second connector 22. As best seen in FIGS. 2 and 4, first connector 20 and second connector 22 are both connected to manifold body 18. First connector 20 is connected to inner lumen 24. Second connector 22 is in fluid communication with outer lumen 26. Thus, manifold body 18 serves to provide for a transition from separate non-coaxial lumens of first connector 20 and second connector 22 to the coaxial lumens that extend through dual lumen portion 14.

Figure 3:
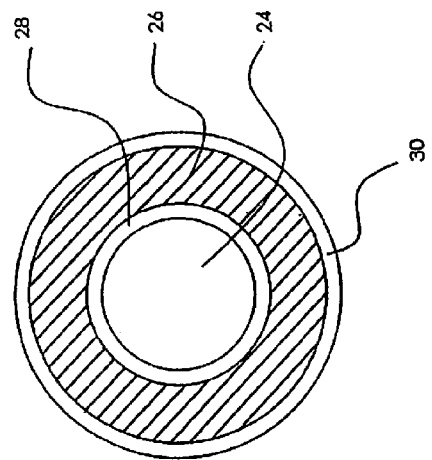
FIG. 3 is a cross sectional view of the coaxial dual lumen pigtail catheter.

Referring to FIG. 3, as indicated above, dual lumen portion 14 defines inner lumen 24 and outer lumen 26. Inner lumen 24 is defined by inner lumen wall 28. Outer lumen 26 is defined by the space between inner lumen wall 28 and outer lumen wall 30. Preferably, inner lumen wall 28 is formed from strong braided diagnostic tubing for high-pressure injections. Desirably, outer lumen wall is formed from thin wall extrusion. Desirably, outer lumen wall has a diameter of at most eight French and preferably seven or six French Inner lumen wall 28, for example, may have an inside diameter at least 0.038 inches to accept a standard guidewire. The inner lumen wall 28 should be sufficient to withstand high pressure injections at pressures up to 1200 pounds per square inch which are utilized in diagnostic procedures.

Referring again to FIGS. 2 and 4, the distal end of dual lumen portion 14 is pierced by at least two side holes 32. Desirably, straight side holes 32 are distributed over an area covering approximately the distal four centimeters of the dual lumen portion 14, to provide for accuracy in measurement.

The juncture 34 between dual lumen portion 14 and single lumen portion 16 desirably includes a gradual taper 36.

Single lumen portion 16 generally includes first straight portion 38, bend 40, second straight portion 42 and pigtail 44. First straight portion 38 desirably extends for about eight centimeters distal from the beginning of taper 36. Desirably, single lumen portion 16 is soft enough to conform to a guide wire and is about five French in diameter.

Bend 40 begins at the distal end of first straight portion 38 and desirably is about 145 degrees. Second straight portion 42 extends distally from bend 40. Second straight portion 42 is pierced by spiral sideholes 46. Desirably, spiral sideholes 46 are distributed over a section of second straight portion 42 about two centimeters in length and are distributed in a spiral pattern that makes at least a substantial portion of one turn around the circumference of second straight portion 42. Preferably, spiral sideholes 46 encircle the second straight portion 42 approximately twice over the desired length.

Pigtail 44 extends distally from the termination of second straight portion 42. Desirably, pigtail 44 is about two centimeters or less in diameter. Pigtail 44 is a spiral coil shape extending around approximately 360 degrees. Desirably, pigtail 44 is sufficiently flexible to be straightened by the passage of a guide wire to allow the pigtail 44 to be passed through the aortic valve and into the left ventricle.

Desirably, the overall length of coaxial dual lumen pigtail catheter 10 is at least 110 centimeters from manifold body 18 to the end of pigtail 44.

Straight side holes 32 are in fluid communication with outer lumen 26. Spiral sideholes 46 are in fluid communication with inner lumen 24.

In operation, coaxial dual lumen pigtail catheter 10 is typically inserted percutaneously into the femoral artery. A guide wire (not shown) is introduced into a puncture in the femoral artery and advanced through the aorta into the left ventricle. The coaxial dual lumen pigtail catheter 10 is advanced along the guide wire while it conforms to the shape of the guide wire and into the left ventricle. The guide wire is then withdrawn, leaving the coaxial dual lumen pigtail catheter in place so that the pigtail 44 resumes its shape in the left ventricle. The second straight portion 42 is in the left ventricle and the first straight portion and dual lumen portion are in the aorta. A pressure measuring device (not shown) of conventional design may then be connected to first connector 20 and second connector 22 to measure the differential pressure between the left ventricle on the proximal side of the aortic valve and the aorta on the distal side of the aortic valve. Simultaneous pressures can be obtained to obtain a diagnostic pressure gradient across the valve by comparing the systolic peaks in the ventricle and the aorta.

In addition, radioopaque fluid may be injected through the inner lumen 26 to perfuse through spiral side holes 46 into the left ventricle. A physician may then observe the flow of radioopaque fluid by fluoroscopy of the heart across the aortic valve.

The pigtail 44 serves both to anchor the single lumen portion 16 within the left ventricle and to present a blunt rounded structure to the internal ventricular wall to reduce the risk of trauma to the ventricular wall.

The present invention may be embodied in other specific forms without departing from the spirit of the essential attributes thereof, therefore, the illustrated embodiments should be considered in all respects as illustrative and not restive, reference being made to the appended claims rather than to the foregoing description to indicate the scope of the invention.

What is claimed is:

1. A method, comprising:
    inserting a catheter having a coaxial dual lumen portion, including an inner lumen and a surrounding outer lumen that share a common axis, and a single lumen portion, including an extension of the inner lumen, into a vascular lumen;
    advancing the catheter through the vascular lumen, including positioning a segment of the single lumen portion, having one or more distal side holes, on a first side of a lesion and positioning a segment of the dual lumen portion, having one or more proximal side holes, on an opposing second side of the lesion;
    fluidly coupling a pressure measuring device to the one or more distal side holes of the single lumen portion and the one or more proximal side holes of the dual lumen portion, thereby operatively coupling the pressure measuring device to the first side of the lesion and the second side of the lesion, respectively;
    obtaining simultaneous pressure measurements from the first side of the lesion and the second side of the lesion; and
    determining a pressure differential across the lesion,
    wherein inserting the dual lumen portion, including the inner lumen and the outer lumen, into the vascular lumen includes inserting exactly two lumens that extend along an entire portion length from a manifold to the single lumen portion.

2. The method of claim 1, wherein inserting the dual lumen portion, including the inner lumen and the outer lumen, into the vascular lumen includes inserting a stronger braided inner tube material surrounded by a thinner-walled outer tube material into the vascular lumen.

3. The method of claim 1, wherein inserting the catheter into the vascular lumen includes inserting a catheter having a collective length of the dual lumen portion and the single lumen portion of at least 110 centimeters.

4. The method of claim 1, wherein inserting the dual lumen portion of the catheter into the vascular lumen includes inserting an outer diameter of six, seven, or eight French into the vascular lumen.

5. The method of claim 1, wherein inserting the single lumen portion of the catheter into the vascular lumen includes inserting an outer diameter of five French into the vascular lumen.

6. The method of claim 1, wherein positioning the segment of the single lumen portion on the first side of the lesion includes positioning a pigtail catheter configuration on the first side of the lesion.

7. The method of claim 6, wherein positioning the pigtail catheter configuration on the first side of the lesion includes anchoring the single lumen portion on the first side of the lesion.

8. The method of claim 6, wherein positioning the pigtail catheter configuration on the first side of the lesion includes presenting a blunt rounded structure to the internal vascular lumen wall.

9. The method of claim 1, wherein positioning the segment of the single lumen portion on the first side of the lesion includes positioning a bend catheter configuration on the first side of the lesion or across the lesion.

10. The method of claim 1, wherein positioning the segment of the single lumen portion on the first side of the lesion includes positioning a first straight catheter configuration, a bend catheter configuration, and a second straight catheter configuration on the first side of the lesion or across the lesion.

11. The method of claim 1, wherein positioning the segment of the single lumen portion on the first side of the lesion includes positioning one or more distal side holes arranged in a spiral configuration on the first side of the lesion.

12. The method of claim 1, wherein positioning the segment of the single lumen portion on the first side of the lesion includes positioning a plurality of distal side holes distributed over approximately two centimeters in length on the first side of the lesion.

13. The method of claim 1, wherein positioning the segment of the dual lumen portion on the second side of the lesion includes positioning a plurality of proximal side holes distributed over approximately four centimeters in length on the second side of the lesion.

14. The method of claim 1, wherein advancing the catheter through the vascular lumen further includes positioning a taper, located between the dual lumen portion the single lumen portion, on the second side of the lesion or across the lesion.

15. The method of claim 1, wherein fluidly coupling the pressure measuring device to the one or more distal side holes of the single lumen portion and the one or more proximal side holes of the dual lumen portion includes coupling a first connector and a second connector, respectively, to the pressure measuring device.

16. The method of claim 1, wherein determining the pressure differential across the lesion includes comparing the pressure measurements on the first side of the lesion and the second side of the lesion.

17. The method of claim 1, wherein determining the pressure differential across the lesion includes measuring a pressure differential across an aortic valve between a left ventricle and an aorta.

18. The method of claim 17, wherein determining the pressure differential across the aortic valve includes comparing one or more systolic peaks in the left ventricle and the aorta.

19. The method of claim 1, wherein determining the pressure differential across the lesion includes using the pressure measuring device to determine a fluid pressure through the inner lumen and determine a fluid pressure through the outer lumen.

20. The method of claim 1, further comprising injecting a diagnostic fluid into the first side of the lesion, including urging the diagnostic fluid through the inner lumen to the one or more distal side holes of the single lumen portion.

21. The method of claim 20, wherein urging the diagnostic fluid through the inner lumen includes urging the diagnostic fluid at a pressure up to 1200 pounds per square inch.

* * * * *